Figure 1:
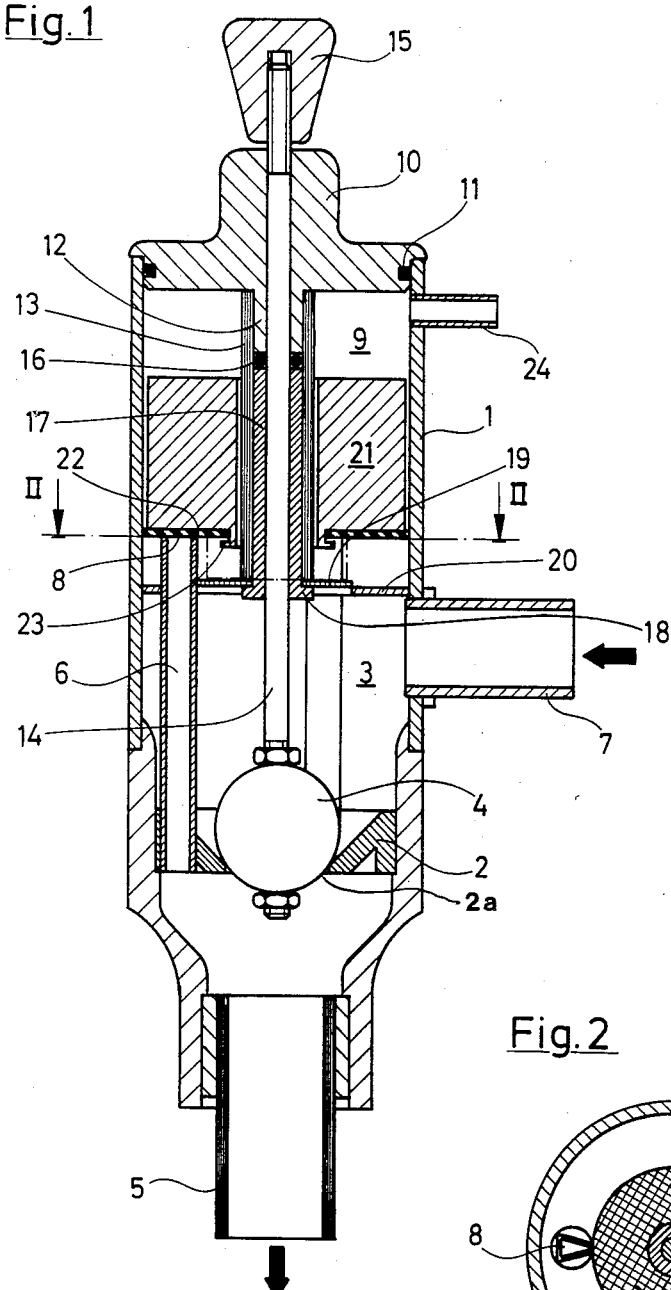

United States Patent [19]

Ernryd

[11] Patent Number: 4,589,442
[45] Date of Patent: May 20, 1986

[54] VALVE FOR SUCTION INSTALLATION

[75] Inventor: Leif Ernryd, Urshult, Sweden

[73] Assignee: Sweden Recycling AB, Urshult, Sweden

[21] Appl. No.: 659,236

[22] Filed: Oct. 9, 1984

[30] Foreign Application Priority Data

Oct. 10, 1983 [SE] Sweden ............................. 8305560

[51] Int. Cl.⁴ .......................................... F16K 21/18
[52] U.S. Cl. .................................. 137/546; 137/398; 137/433; 210/125; 433/92
[58] Field of Search ............... 210/123, 125; 137/546, 137/430, 433, 397, 398; 433/92

[56] References Cited

U.S. PATENT DOCUMENTS

| 1,157,643 | 10/1915 | Kuhn | 137/546 |
| 2,742,156 | 4/1956 | Spongler | 210/125 |
| 2,821,021 | 1/1958 | Winter | 433/92 |
| 3,187,895 | 6/1965 | Pall et al. | 210/123 |
| 3,305,927 | 2/1967 | Mitchell | 433/92 |
| 3,746,033 | 7/1973 | Keiper, II | 433/92 |

FOREIGN PATENT DOCUMENTS 618312 3/1926 France ............................. 210/125

Primary Examiner—A. Michael Chambers
Attorney, Agent, or Firm—Browdy and Neimark

[57] ABSTRACT

A valve for a suction system, which comprises a sedimentation chamber (3) for collection of particles contained with the liquid sucked into the valve and suction outlet (6) having suction openings (8) in a float house (9), which suction openings (8) cooperate with a membrane (22), which is attached to a float member (21) in the float house (9) so that the membrane seals against the suction openings (8) when liquid do not reach the float house (9) and so that the area of the suction openings (8) is successively uncovered when the membrane (22) moves with the float member (21) at rising liquid level in the float house (9).

12 Claims, 2 Drawing Figures

VALVE FOR SUCTION INSTALLATION

The present invention relates to a valve, which preferably is intended to be used in a suction line for suction draining of a liquid, which sometimes can contain particles, and which valve comprises membrane means which in absence of liquid to be drained by suction force from the suction line seals against openings to an outlet passage through the valve, while in presence of liquid to be drained opens for transport of liquid from an inlet in the valve to said outlet passage.

TECHNICAL BACKGROUND

In suction systems for sucking off liquid being supplied to the system intermittently, there is often need for a valve which opens for a liquid flow while it closes for air suction when the liquid flow ceases. This automatic vacuum interruption on the inlet side of the valve can be desirable from several aspects. One aspect is to minimize the gas intake in the suction installation, and another aspect is to eliminate the suction sound caused by the vacuum. The elimination of a disturbing suction sound is of particular interest within the dental surgery field, and therefore in the following description it is referred to this field in particular, even if the invention is generally applicable within several other technical fields.

At dental surgery installations there is today desirable and in some countries even required through legislation to connect all sewer facilities for e.g. spittoones and suction equipment to an amalgam separation unit before discharge in general sewer systems. Since several dental surgery equipments are often located in the same place at dental treatment-centres comprising several sewer facilities, it is from practical and economic point of view preferable to use a central plant in a separate room, such as a basement room, for vacuum pump, amalgam separator and liquid separator. When such a central plant serves a number of dental surgery units, it is realized that manual on-off control of the vacuum pump is an impossible way to eliminate disturbing suction sound from for example a so called spittoon at a dentist's chair when the liquid supply (rinse water) to the same is shut off. Manually operated valves with an "on"-position for sucking off liquid and an "off"-position for shutting off the suction sound cannot be accepted, since the liquid is so frequently supplied that the valve must be operated very often to prevent liquid overfill, alternatively disturbing suction sounds on the inlet side of the valve, that is in the spitoone.

TECHNICAL STANDPOINT

Therefore, some kind of automatic operating valves are used today to shut off the suction sound. For example there is used for this purpose valves having liquid controlled or air pressure controlled membranes which in their turn act on a valve body to move with respect to a valve seat. One difficulty with such valves is to provide from existing dental surgery equipments adequate control signal function. Further, there is risk for leakage at the membrane and thereby operation disturbances. Even if said disturbances or control signal problems do not occur, these valves are either completely closed or completely open and can thus not provide successive and automatic adjustment to the water flow passing through them, and in practice a quite distinct suction sound is generated when the liquid flow has passed and before the control signal closes the valve.

In a valve specially designed for dental surgery installations to cut off the suction air stream, there is utilized the principle of applying a thin membrane over a surface element provided with two apertures, whereat liquid is sucked up through one aperture and passes between the membrane and the surface element on to the other aperture. Due to presence in the liquid of particles of a size up to several mm, there is an obvious risk for particle stagnation in the liquid passage along the membrane which impairs the sealing function of the valve when closed. Further, the valve requires for its operation the build-up of a liquid column on its inlet side, and therefore it is installed in the floor box of the dental surgery unit and generally requires professional attendance at impaired valve function.

THE INVENTION

One object of the invention is to achieve a valve which automatically opens exactly when and only when liquid is to be passed through the suction line without generation of disturbing suction sounds and which valve is not afflicted by said risk for impaired sealing function due to particle clogging along the membrane sealing area. A further object of the invention is to achieve a valve of such a simple design and such an accessibility that any need of proffessional service is completely eliminated.

These objects have been achieved by a valve of the kind introductively mentioned, which valve primarily is characterized in that its inlet communicates with a sedimentation chamber for collection of particles accompanying the liquid and that a float member is provided in a float house being in communication with said sedimentation chamber, which float member is connected to said membrane means so that the membrane means at a certain liquid level in the float house is brought in a position which opens for liquid flow between said inlet and an outlet passage of said valve.

A combination of a particle separation chamber and a float member controlled membrane function eliminates the risk for disturbances in the sealing function, simultaneously as the opening impulse acting on the membrane means is related to the velocity with which the liquid rises in the float house, which provides a successive adjustment of the opening procedure to the liquid flow.

According to a preferred embodiment of the invention, an extremely smooth and successive opening procedure is achieved by connecting the membrane means with the float member so that the outlet area sealed by the membrane means is successively uncovered for liquid passage simultaneously as the float member moves upwards a certain distance in the float house. This successive uncovering of the total sealing area eliminates the typical and in the context inconvenient "on"-"off"-characteristics, which is obtained if the opening procedure cannot be started until such an opening force is exerted on membrane means that balances the suction force acting on the entire opening area.

A successive uncovering of the opening area can in theory be carried out in may different ways. According to a further preferred embodiment of the invention, the membrane means is fixed to the float member so that part of the membrane surface is freely movable with respect to the float member. By localizing the free part of the membrane means straight above the openings to be sealed while a part of the membrane means which is fixed to the float member is located to the side of the outlet openings, successive release between the membrane element and the sealing surface from one end of the individual outlet opening is caused.

Figure 2:
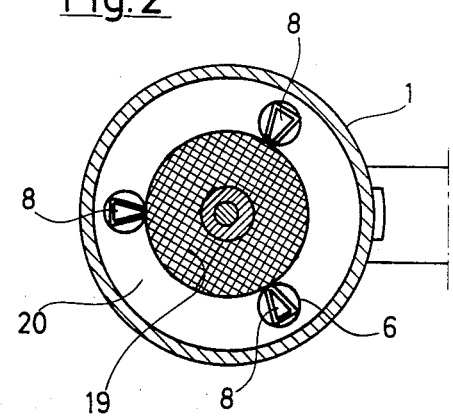

The invention will now be further described by means of a preferred embodiment of the same and with reference to the accompanying drawings, in which FIG. 1 shows a vertical section through the valve and FIG. 2 shows a horizontal section through the valve of FIG. 1.

In the preferred embodiment according to FIG. 1, the valve comprises a cylindric valve housing 1 intended to be located in operation with its centre axis in vertical position. In the lower part of the cylindric housing an insert element 2 constitutes bottom and a valve seat 2a for a sedimentation chamber 3, the valve seat 2a cooperating with a valve body 4 for opening and closing the sedimentation chamber 3 with respect to an outlet and suction line connection 5 arranged at the bottom of the valve housing. The insert element 2 further comprises tubular passages 6, the lower parts of which penetrate the bottom of the sedimentation chamber and communicate with the outlet 5, and which extend through the sedimentation chamber 3 up above an inlet tube piece 7 and end in horizontally located openings 8 in an upper part of the valve housing constituting a float house 9.

The top of the valve housing 1 or the float house 9 is closed by a top element 10, which seals against the valve housing by means of a O-ring 11. The central part of the top element 10 has a projecting tubular piece 12 around which a sleeve member 13 is fixed. A pull rod 14 is arranged through the top element 10 and the tubular piece 12. The lower end of the pull rod is fixed to the valve body 4 and the upper end above the top element 10 is provided with a pull handle 15. To seal off the clearance space between the pull rod 14 and the top element 10 an O-ring 16 is fixed in the sleeve member 13 between the tubular piece 12. A further tube element 17 is pressed from below into the sleeve member 13 to provide, like the tubular piece 12, continued guidance with clearance for the pull rod 14. Between a flange 18 at the lower end of the tube element 17 and the sleeve member 13 an annular net element 19 is fastened, the net element serving as filter for particles which do not settle immediately in sedimentation chamber 3 and have a tendency to accompany the liquid flow up into the float house 9. To block the entire cross section of the valve housing 1, an annular cover element 20 is arranged below the end openings 8 of the tubular passages 6 and is made in one piece with the insert element 2 at the embodiment shown.

Around the central sleeve element 13 a hollow cylindric float member 21 is guided. On the underside of the float member an annular membrane 22 is fixed at its central part by means of a collar element 23 of the float member 21. The outer part of the membrane 22 is freely movable with respect to the float member 21 and extends across the openings 8 of the tubular passages 6. In the upper part of the float house 9 an air outlet 24 is arranged for balancing the air pressure in the float house as the liquid supplied through the inlet tube 7 rises or falls while drained through the tubular passages 6.

FIG. 2 shows a horizontal section through the valve housing at the level of the openings 8 of the tubular passages 6 a preferred embodiment of the openings 8. These have the form of triangles with a triangle apex directed towards the centre. In this way it is achieved that the area of the openings 8 increases progressively in direction towards the periphery of the valve housing, which arrangement further contributes to a successive and discreet release between the openings and the membrane 22, the inner part of which that is fixed to the float member starting its upward movement with the float member, while the major part of the membrane through the suction force in the tubular passages 6 still covers the major part of the openings 8.

The use and operation of the valve described above is as follows. The inlet tube 7 is connected for example to a spittoon outlet in a dental surgery equipment and the outlet tube 5 is connected to a suction line system. Sludge material accompanying the water from the spittoon outlet, such as amalgam particles, settle and fall to the bottom of the sedimentation chamber 3. When the water level reaches the float member 21, the latter starts to rise upwards in the float house 9 and brings with it the membrane 22 which successively leaves its contact with the suction passages 6 from the inner end of the openings 8. At a slow liquid flow rate only a smaller part of the openings 8 are uncovered, while at larger flow rates the float member 21 rises to a higher position so that a larger part of the openings 8 are uncovered. Hereby it is realized, that the openings 8 are uncovered successively so that any kind of turbulence generating shock opening never occurs. Due to the fact that all heavy and larger particles settle directly in the sedimentation chamber and the more poorly settling particles are further obstructed by the central net element 19 and the cover element 20, only very fine and for the sealing function of the membrane 22 against the openings 8 unharmful particles will continuously accompany the liquid flow through the tubular passages 6 out through the valve outlet 5. The amount of particles collected on the bottom of the sedimentation chamber 3 is discharged, when required, through the outlet 5 by pulling the handle 15 of the pull rod 14. In the use of the valve at a dental surgery unit such a manual operation once a day may be quite sufficient. The discharge of collected particles should suitably be combined with plentyfull flushing in the spittoon so that any possible settling of particles in the suction line is prevented.

In addition to the preferred embodiment of the valve according to the invention shown above, it is realized that several alternative design details are possible within the scope of the attached patent claims. When so is suitable, for example the suction passages 6 and the bottom outlet from the sedimentation chamber 3 can be connected to separate outlet conduits, for example in order to discharge the liquid flow through the passages 6 through a general sewer, while the particles from the sedimentation chamber 3 are brought to a special separation device or tank. Further, the sealing function between the float member carried membrane element and the suction openings can be arranged in several different ways within the scope of the patent claims. In case of using an annular membrane, the membrane can be attached to the float member at its peripheral part while sealing against the suction openings occurs at an inner freely moving part of the membrane. Further, a number of suction openings of varying size can be arranged in a surface plane cooperating with the membrane so that the membrane first leaves the contact with a number of smaller openings and after that, in case of a larger liquid flow, also leaves its contact with further, possibly larger separate openings.

The manual operation of the bottom valve of the sedimentation chamber 3 can, if so found suitable, also be carried out automatically, for example by means of a time controlled manoeuvre system.

I claim:

1. A valve for use with the suction line of apparatus for automatic draining of a liquid from a valve housing wherein the liquid may contain particles, the valve comprising:
   a cylindrical enclosure including upper, middle, and lower chambers, and annular means for dividing said housing into said chambers,
   first means for communicating the lower chamber with said suction line,
   second means for communicating said middle chamber with a source of said liquid,
   at least one tubular means each having one end communicating with said lower chamber and an opposite end communicating with said upper chamber,
   float means supported in said upper chamber for movement in the axial direction of said enclosure, said float means being movable between one position in which said tubular means opposite end is blocked, and other positions in which said tubular means opposite end is blocked, and other positions in which said tubular means opposite end is unblocked, and
   an annular membrane having a portion thereof fixed to said float means, said membrane normally covering said tubular means opposite end when said float means is in said one position,
   whereby suction in said suction line causes said liquid to enter said middle chamber, and when said liquid fills said middle chamber and rises above the annular means dividing said upper chamber from said middle chamber, the float means is raised from said one position whereupon said membrane uncovers at least a portion of said tubular means opposite end so that said liquid can flow into and through said tubular means to said suction line.

2. The valve of claim 1,
   wherein said annular dividing means comprises a first divider separating said upper chamber from said middle chamber and a second divider separating said middle chamber from said lower chamber, said first divider including means for filtering particles from said liquid as said liquid flows from said middle chamber into said upper chamber, and said second divider including an opening normally blocked by manually operable valve means.

3. The valve of claim 1, wherein
   each tubular means has a cross-sectional area which increases in proportion to the radial distance from the axis of said cylindrical enclosure,
   whereby as said float means rises in said upper chamber, a proportionately larger area of said tubular means opposite end is uncovered by said membrane means.

4. A valve according to claim 1, wherein the opposite end of each of said tubular means constitutes an opening of non-circular cross-sectional area, and said membrane successively uncovers the outlet area of said openings, which the membrane normally covers when said float is in said one position, to permit more of said liquid to flow as the float means moves upwards.

5. A valve according to claim 4, wherein said membrane includes one part attached to the float means only along a part of the membrane surface which is not in position for sealing against said openings, while another part of said membrane surface, in position for sealing against each said opposite end, is freely movable with respect to the float means.

6. A valve according to claim 5, wherein the uncovered area of said openings increases progressively with the distance from the part of the membrane which is attached to the float means.

7. A valve according to claim 5, wherein the upper chamber comprises means for limiting the downward movement of the float means, said openings are disposed at a predetermined radial distance from the central axis of said cylindrical enclosure, and said membrane is attached to the float means radially inside said openings and is free with respect to the float means above said openings.

8. A valve according to claim 7, wherein said membrane is attached to the float means at a radially inner part thereof, and has its peripheral part, which cooperates with said openings, freely movable with respect to the float means.

9. A valve according to claim 1, wherein a bottom valve is arranged in the bottom of said middle chamber for intermittent opening and discharge of collected particles.

10. A valve according to claim 9, wherein said bottom valve comprises a manually operable valve body, which cooperates with an outlet opening in the bottom of the sedimentation chamber, and said valve body being connected to a control member which extends out through the enclosure for manual opening of the bottom valve and discharge of collected particles through said outlet opening.

11. A valve according to claim 10, wherein a tube element extends vertically through said upper chamber, within which said control member is movable and guided through at least one fixed sealing ring and which tube element simultaneously serves as guide element for the float means, the latter including a central through-hole arranged around said tube element.

12. A valve according to claim 1, wherein the outlet for discharge of the particles collected in the sedimentation chamber as well as said openings, which cooperate with the membrane for draining of liquid freed from particles, communicate with a common valve outlet, which is connected to said suction line.

* * * * *